United States Patent
Lu et al.

(10) Patent No.: US 12,350,460 B2
(45) Date of Patent: Jul. 8, 2025

(54) ELECTRO-RESPONSIVE SILK FIBROIN MATERIAL, ELECTRO-RESPONSIVE SILK FIBROIN MICRONEEDLE, INSULIN MICRONEEDLE PATCH HAVING ELECTRO-RESPONSIVE SILK FIBROIN AND PREPARATION METHOD THEREFOR, AND TRANSDERMAL DRUG DELIVERY DEVICE

(71) Applicant: Pharsun Medical Biotechnics (Shanghai) Co., Ltd., Shanghai (CN)

(72) Inventors: Shenzhou Lu, Jiangsu (CN); Zhenzhen Qi, Jiangsu (CN); Xiaosheng Tao, Jiangsu (CN); Shijie Guo, Jiangsu (CN); Zheng Yan, Jiangsu (CN); Yujian Li, Jiangsu (CN)

(73) Assignee: Pharsun Medical Biotechnics (Shanghai) Co., Ltd., Shanghai (CN)

( * ) Notice: Subject to any disclaimer, the term of this patent is extended or adjusted under 35 U.S.C. 154(b) by 0 days.

(21) Appl. No.: 18/886,923

(22) Filed: Sep. 16, 2024

(65) Prior Publication Data
US 2025/0001153 A1   Jan. 2, 2025

Related U.S. Application Data

(63) Continuation of application No. PCT/CN2023/080804, filed on Mar. 10, 2023.

(30) Foreign Application Priority Data

Mar. 16, 2022  (CN) .................. 202210258571.X
Mar. 16, 2022  (CN) .................. 202210263237.3

(51) Int. Cl.
*C07K 14/435*  (2006.01)
*A61M 37/00*  (2006.01)

(52) U.S. Cl.
CPC ... *A61M 37/0015* (2013.01); *C07K 14/43586* (2013.01); *A61M 2037/0053* (2013.01)

(58) Field of Classification Search
CPC ...... A61M 37/0015; A61M 2037/0053; C07K 14/43586
See application file for complete search history.

(56) References Cited

FOREIGN PATENT DOCUMENTS

| CN | 111588913 A | 8/2020 |
|---|---|---|
| CN | 111632198 A | 1/2022 |

(Continued)

OTHER PUBLICATIONS

Magaz et al., Electroresponsive Silk-Based Biohybrid Composites for Electrochemically Controlled Growth Factor Delivery, 2020, Pharmaceutics, 12, 742. (Year: 2020).*

(Continued)

*Primary Examiner* — Robert B Mondesi
*Assistant Examiner* — Naghmeh Nina Moazzami
(74) *Attorney, Agent, or Firm* — Schwegman Lundberg & Woessner, P.A.

(57) ABSTRACT

A method for preparing an electro-responsive silk fibroin material comprises: (1) activation of silk fibroin, (2) thiolation of silk fibroin, which involves: adding a cysteamine hydrochloride solution dropwise to the activated silk fibroin solution, adjusting the pH value of the final solution to 5-6, performing a reaction under stirring at 0° C.-4° C., taking out the resulting product, and then leaving the resulting product to stand for a reacting at 2° C.-8° C. to obtain a thiolated silk fibroin; (3) purification of the thiolated silk fibroin; and (4) preparation of an electro-responsive silk fibroin material, which involves: taking the purified thiolated silk fibroin solution, pouring same in a mold, drying same after defoaming, and demolding same to obtain the electro-responsive silk fibroin material.

5 Claims, 3 Drawing Sheets

(56) References Cited

FOREIGN PATENT DOCUMENTS

| CN | 113975461 A | 1/2022 |
|----|-------------|--------|
| CN | 114699511 A | 7/2022 |
| CN | 114921105 A | 8/2022 |
| WO | WO-2023/174176 A1 | 9/2023 |

OTHER PUBLICATIONS

Chinese Patent Application No. 202210258571.X, First Office Opinion Notice, with English translation, 10 pgs.
Chinese Patent Application No. 202210258571.X, Notice of Grant of Invention Patent Right, with English translation, 2 pgs.
International Patent Application No. PCT/CN2023/080804, International Search Report and Written Opinion, with English translation of ISR, 9 pgs.
Li, Y., "Preparation of disulfide cross-linked reduction-responsive hydrogels and microgels and their application in controlled drug release", China Excellent Master's Thesis Database, Engineering Technology Series I, No. 3, B016-1044, 75 pgs., abstract in English, (May 15, 2017).
Zhang, X., et al., "Thiolation and characterization of regenerated Bombyx mori silk fibroin films with reduced glutathione", BMC Chemistry, vol. 13, No. 62, (May 10, 2019), 9 pgs.

* cited by examiner

ELECTRO-RESPONSIVE SILK FIBROIN MATERIAL, ELECTRO-RESPONSIVE SILK FIBROIN MICRONEEDLE, INSULIN MICRONEEDLE PATCH HAVING ELECTRO-RESPONSIVE SILK FIBROIN AND PREPARATION METHOD THEREFOR, AND TRANSDERMAL DRUG DELIVERY DEVICE

CLAIM OF PRIORITY

This application is a continuation of International Application No. PCT/CN2023/080804, filed on Mar. 10, 2023, and published as WO 2023/174,176 A1 on Sep. 21, 2023, which claims the benefit of priority under 35 U.S.C. § 119 to Chinese Patent Application No. 202210258571.X, filed on Mar. 16, 2022, and to Chinese Patent Application No. 202210263237.3, filed on Mar. 16, 2022, each of which is incorporated by reference herein in its entirety.

TECHNICAL FIELD

The present disclosure relates to the technical field of silk fibroin microneedle patch and medical materials and cosmetic materials, and in particular to a method for preparing a silk fibroin material whose internal pore diameter increases after being electrified, an electro-responsive silk fibroin material prepared by the preparation method, an electro-responsive silk fibroin microneedle based on the electro-responsive silk fibroin material, an electro-responsive silk fibroin insulin microneedle patch and a preparation method thereof, and a transdermal drug delivery device based on the above material.

BACKGROUND

The field of intelligent responsive drug delivery is a hot topic in the current research of materials science and biomedicine. Based on the effects of electric field, current, magnetic field, light and mechanical external force, changes in pH value, temperature and other stimuli can make drugs responsively delivered into the body. However, how to control the drug delivery method so that intelligent responsive drug delivery is convenient to use, effectively delivered and accurately control the dosage is a challenge.

Microneedle transdermal drug delivery is a method that uses a microneedle array less than 1 mm in length to pierce the epidermis of the skin and form micropores to improve the efficiency of transdermal drug delivery. It can easily, painlessly, safely and conveniently achieve drug delivery, and is playing an important role in the field of intelligent drug delivery. At the same time, since the microneedle array is attached to the skin during use, it can effectively accept external stimuli, especially current, electric field and magnetic field to achieve controlled release of drugs.

Silk fibroin is a green natural bio-based material with low immunogenicity, excellent biocompatibility and outstanding mechanical properties. With the development of modern science and technology, silk is no longer limited to the textile field, and has been widely used in the field of drug delivery. However, the drug-loaded silk fibroin microneedles do not have intelligent responsiveness, which is determined by the structure of silk fibroin. Due to the lack of corresponding stimulus-responsive groups or too few responsive groups on the silk fibroin molecules. On the whole, pure silk fibroin does not have stimulus-responsive changes, so it cannot be used for intelligent drug delivery.

In order to solve the above problems, Chinese disclosure patent CN108047466A discloses a method for preparing silk microneedles, in which the chemical crosslinking agent used is glutaraldehyde, and then the silk solution after chemical crosslinking is made into microneedles; after the microneedles are made, water vapor treatment is carried out to obtain high-strength silk microneedles, which can easily penetrate the skin and can be mixed with a large amount of drugs. However, this microneedle is treated with water vapor, and the internal structure is dominated by β-folding, which is not easy to absorb water and swell, resulting in slow drug release, low drug release rate, and lack of responsiveness; at the same time, glutaraldehyde, as a crosslinking agent, is more harmful to the human body and can stimulate the skin and digestive system. Another example is Chinese disclosure patent CN102580232B, which discloses a silk microneedle system and silk nanoparticles and a method for preparing the same. The silk fibroin microneedles prepared by this method dissolve rapidly after piercing the skin, thereby releasing nanoparticles. However, this microneedle system releases the drug into the body at one time, and cannot control the intelligent release and release amount of the drug.

Electro-assisted drug delivery is cheap and easy to implement, and can help drugs overcome tissue barriers and enter the body. Its drug release mechanism is mainly electroporation and iontophoresis therapy, etc. However, these methods all use some large currents or electric fields, which will bring certain safety risks. How to complete the intelligent responsive delivery of drugs in silk fibroin microneedles under low current or electric field is very meaningful, which can greatly expand the precise, convenient and safe application of intelligent drug delivery in the human body.

Gu et al. [Nature Biomedical Engineering, 2020, 4 (7): 1-8.] developed a method for a glucose-responsive N-vinylpyrrolidone-based microneedle patch, which contains a copolymer designed for glucose-triggered insulin delivery. This microneedle has a large drug loading and has an intelligent response effect, which can be used for insulin closed loop delivery. However, the microneedle substrate is prepared using polymer materials, which is less biosafety and green sustainability. At the same time, the intelligent response speed of glucose is slow and cannot be quickly responded to and released.

As another example, Moonjeong et al. [DOI: 10.1038/s41598-020-58822-w] developed a multifunctional system composed of hyaluronic acid microneedles as an effective transdermal delivery for rapid local drugs. Under the action of ultrasound, the microneedle will induce the dissolution of hyaluronic acid by sound pressure vibration, and the alternating current iontophoresis therapy can improve the diffusion of hyaluronic acid ions and rhodamine driven by electrostatic force. This method has a fast drug release rate and can be used for rapid local drug delivery. However, due to the use of a higher voltage electric field directly acting on the drug or human skin, this will bring certain risks of drug deterioration and human harm, and has certain limitations in use.

Hence, how to develop an electro-responsive material that can be acted on a microneedle, realize the rapid intelligent responsiveness change of the material through low voltage electrical stimulation, and then control the rapid response release of the drug, and complete the release of electro-responsive intelligent drugs is crucial.

SUMMARY

In view of this, in order to overcome the defects of the prior art, one objective of the present disclosure is to provide a method for preparing an electro-responsive silk fibroin material, wherein the prepared silk fibroin material and silk fibroin microneedle can control the pore size in the material by switching electricity and achieve the purpose of controlling the drug release rate.

To achieve the above objective, the present disclosure adopts the following technical solutions:

A method for preparing an electro-responsive silk fibroin material, comprising:

(1) activation of silk fibroin: diluting an aqueous solution of silk fibroin to a concentration of 20-30 mg/mL, then placing the solution in an ice bath to stabilize the temperature to 0-4° C., and adjusting the pH value of the silk fibroin solution to 5-6 using a buffer solution; adding 1-10 wt % of N-hydroxysuccinimide relative to the mass of the silk fibroin to the silk fibroin solution, and then adding 2-20 wt % of 1-(3-dimethylaminopropyl)-3-ethylcarbodiimide hydrochloride relative to the mass of the silk fibroin, mixing uniformly and performing a reaction for 0.4-1 h to obtain an activated silk fibroin solution; Activate the carboxyl groups on the silk fibroin with NHS and EDC to make it easier to react with the amino group for subsequent grafting of cysteamine and silk fibroin, and maintain the biocompatibility of the silk fibroin;

(2) thiolation of silk fibroin: adding a cysteamine hydrochloride solution dropwise with a concentration of 40-60 mg/mL to the activated silk fibroin solution, and making the cysteamine hydrochloride concentration in the final solution be 20-80 mmol/L, and then adjusting the pH value of the final solution to 5-6 using a buffer solution; performing a reaction under stirring at 0-4° C. for 2-5 h, and then taking out the resulting product and leaving the resulting product to stand for a reacting at 2-8° C. for 8-10 h to obtain a thiolated silk fibroin solution;

(3) purification of thiolated silk fibroin: placing the silk fibroin solution after the reaction in a dialysis bag for dialysis; centrifuging and taking the supernatant to obtain the purified thiolated silk fibroin solution after the dialysis is completed;

(4) preparation of electro-responsive silk fibroin material: taking the purified thiolated silk fibroin solution, and pouring the purified thiolated silk fibroin solution in a mold, and evacuating in a vacuum drying oven to remove air bubbles; then placing the defoamed mold in a constant temperature and humidity environment for drying, and obtaining the electro-responsive silk fibroin material after drying and demolding. As for what shape the electro-responsive silk fibroin material is made into, the mold can be designed according to actual needs, and then the silk fibroin material of the corresponding shape can be prepared, such as preparing an electro-responsive silk fibroin microneedle patch.

According to some preferred embodiments of the present disclosure, the electro-responsive silk fibroin material contains silk fibroin and thiol groups grafted on the silk fibroin; the content of the thiol groups is 20-100 μmol/g. The thiol content is too low, the electro-responsiveness is small, and the swelling degree does not change much. On the other hand, the carboxyl content in the silk fibroin molecule is limited, and the control of the above reaction conditions is also to insert the thiol groups on the carboxyl groups that can react as much as possible to increase the content of the thiol groups, so as to achieve better electrical response effect and swelling degree control.

According to some preferred embodiments of the present disclosure, the silk fibroin material has current responsiveness, and the swelling rate is 50-120% in one hour when not powered on, and the swelling rate is 120-250% when powered on at a voltage of 0.6 V for one hour. The redox potential between the thiol and the disulfide bond is about 0.6 volts. The voltage cannot be higher than 1 volt to prevent the electrolysis of water. Below 0.6 volts, the disulfide bond cannot be reduced. In actual application, the voltage can be set between 0.6-0.9 volts. The current responsiveness of the present disclosure refers to the change in the performance (swelling rate) of the prepared silk fibroin material before and after power on, and the swelling rate of the material after power on is significantly improved compared with the swelling rate without power on.

According to some preferred embodiments of the present disclosure, the mass ratio of the N-hydroxysuccinimide to the silk fibroin is 1:100-1:10; the mass ratio of the 1-(3-dimethylaminopropyl)-3-ethylcarbodiimide hydrochloride to the silk fibroin is 1:50-1:5; the mass ratio of the cysteamine hydrochloride to the silk fibroin is 1:100-1:2.5.

According to some preferred embodiments of the present disclosure, the sodium thiosulfate is added to the deionized water for dialysis and an inert gas is introduced for protection during the dialysis; the deionized water with added sodium thiosulfate is replaced every 2-4 h, and the dialysis procedure 2d is repeated and the inert gas protection is maintained; then the deionized water without added sodium thiosulfate is used for dialysis 1d. The inert gas is preferably nitrogen $N_2$.

According to some preferred embodiments of the present disclosure, the concentration of the sodium thiosulfate in deionized water is 0.001-0.0015 mol/L.

According to some preferred embodiments of the present disclosure, the molecular weight cutoff of the dialysis bag used during dialysis is 8-14 kDa.

According to some preferred embodiments of the present disclosure, the constant temperature and humidity conditions are 20-30° C. and 55-65% relative humidity.

According to some preferred embodiments of the present disclosure, the buffer solution is one selected from 2-(N-morpholino) ethanesulfonic acid, glycine-hydrochloric acid, citric acid-sodium citrate, acetic acid-sodium acetate, potassium hydrogen phthalate-sodium hydroxide, and Tris-hydrochloric acid buffer.

According to some preferred embodiments of the present disclosure, the silk fibroin aqueous solution is obtained from silkworm silk through degumming, dissolution and dialysis.

The second objective of the present disclosure is to provide an electro-responsive silk fibroin material prepared by the preparation method described above.

The third objective of the present disclosure is to provide an electro-responsive silk fibroin microneedle, which uses the thiolated silk fibroin as described above, pours it in a microneedle mold, and removes air bubbles by vacuuming in a vacuum drying oven; then the defoamed mold system is placed in a constant temperature and humidity environment for drying, and an electro-responsive silk fibroin microneedle patch is obtained after drying and demolding.

Preferably, the present disclosure provides a method for preparing an electro-responsive silk fibroin insulin microneedle patch. The prepared silk fibroin insulin microneedle patch can control the pore size in the material by switching electricity and achieve the purpose of controlling the insulin release rate in the microneedle, thereby realizing intelligent insulin release.

In some embodiments, a method for preparing an electro-responsive silk fibroin insulin microneedle patch with, comprising:
(1) activation of silk fibroin, (2) thiolation of silk fibroin, (3) purification of thiolated silk fibroin; these three steps are the same as the steps in the preparation method of an electro-responsive silk fibroin material described above, and will not be described in detail here;
(4) preparation of insulin solution: putting insulin in a centrifuge tube, adding 0.01M-0.05M hydrochloric acid solution and mixing well to fully dissolve insulin, so that the concentration of insulin in the solution is 10-50 mg/mL; then adding 0.01M-0.05M buffer solution, and adjusting the pH value of the solution to 6.7-7.4 to form an insulin solution;
(5) preparation of mixed solution: taking the insulin solution prepared in the above steps, adding it to the thiolated silk fibroin solution and stirring well, so that the concentration of thiolated silk fibroin in the mixed solution is 10-40 mg/mL, and the concentration of insulin is 1-10 mg/mL; and controlling the drug loading of the microneedles to prevent excessive drug loading from causing insulin precipitation and reducing the strength of the microneedles;
(6) preparation of insulin microneedle patch: taking the mixed solution and pouring it in the microneedle mold, and evacuating in a vacuum drying oven to remove air bubbles, then placing the defoamed mold in a constant temperature and humidity environment for drying, and obtaining the electro-responsive silk fibroin insulin microneedle patch after drying and demolding.

According to some preferred embodiments of the present disclosure, the insulin content in the silk fibroin insulin microneedle patch is 10-100 mg/g, and the thiol content is 10-100 μmol/g. The thiol content is too low, the electro-responsiveness is small, and the swelling degree does not change much. On the other hand, the carboxyl content in the silk fibroin molecule is limited, and the control of the above reaction conditions is also to insert the thiol groups on the carboxyl groups that can react as much as possible to increase the content of the thiol groups, so as to achieve better electrical response effect and swelling degree control.

The fourth objective of the present disclosure is to provide an electro-responsive silk fibroin insulin microneedle patch prepared by the preparation method as described above. In the silk fibroin insulin microneedle patch, the mass ratio of silk fibroin and insulin is 4-20:1. The electro-responsiveness is achieved by switching on a DC power supply; by energizing the silk fibroin insulin microneedle patch, the swelling degree of the silk fibroin insulin microneedle patch is increased, thereby accelerating the release of insulin. The electro-responsive silk fibroin insulin microneedle patch can achieve changes in swelling degree under low voltage (voltage below 1V) stimulation, has high swelling characteristics under powered on conditions, and has low swelling characteristics when not powered on, thereby achieving controlled release of insulin. At the same time, the microneedle transdermal patch avoids the first-pass effect of the liver and can improve the bioavailability of the drug.

The fifth objective of the present disclosure is to provide a transdermal drug delivery device, which can reduce components while ensuring perfect functions, and make the voltage loaded on the microneedle patch controllable, so as to achieve the purpose of controlling the intelligent transdermal drug release of macromolecular drugs. Specifically, the transdermal drug delivery device includes a power supply, a switch, a fixed resistor, an adjustable resistor and a microneedle patch containing a drug, and the power supply, the switch and the adjustable resistor constitute a main circuit; the fixed resistor is connected in parallel with the microneedle patch and then connected in series to the main circuit, and the microneedle patch is a conductive microneedle patch; the microneedle patch is used to release the drug outward when powered on; the microneedle patch is an electro-responsive silk fibroin insulin microneedle patch as described above. By setting an adjustable resistor, the voltage loaded on the microneedle patch can be adjusted, and at the same time, a fixed resistor is set to ensure safe use. The microneedle patch is a drug carrier and can also achieve conductivity.

According to some preferred embodiments of the present disclosure, the power supply is a DC power supply.

According to some preferred embodiments of the present disclosure, the voltage of the power supply is 3V~3.6V.

According to some preferred embodiments of the present disclosure, the power supply is a 3V~3.6V rechargeable button-type lithium-ion battery, or a non-rechargeable 3V button-type lithium-manganese battery.

According to some preferred embodiments of the present disclosure, the resistance of the fixed resistor is 200-600Ω, preferably 500Ω.

According to some preferred embodiments of the present disclosure, the adjustable resistor has a resistance adjustment range of 200-2000Ω.

According to some preferred embodiments of the present disclosure, the fixed resistor and the adjustable resistor are used to maintain the voltage loaded on the microneedle patch within a safe voltage.

According to some preferred embodiments of the present disclosure, the safety voltage is 0.6~1V. The safety voltage needs to ensure safety in use and cooperate with the microneedle patch to achieve response.

According to some preferred embodiments of the present disclosure, an alarm component is provided on the main circuit, and the alarm component is an indicator light and/or a buzzer.

The above-mentioned transdermal drug delivery device uses fewer components and occupies less space when combined with the terminal, which can realize the miniaturization and portability of the corresponding product. At the same time, it can make the voltage loaded on the microneedle patch adjustable, and realize the controlled release of drugs in combination with the microneedle patch.

The reaction principle of the present disclosure is as follows: the thiol modification of silk fibroin is prepared by coupling reaction of silk fibroin and cysteamine hydrochloride using N-hydroxysuccinimide/1-(3-dimethylaminopropyl)-3-ethylcarbodiimide hydrochloride system. In the initial stage of the reaction, 1-(3-dimethylaminopropyl)-3-ethylcarbodiimide hydrochloride (EDC) reacts with the carboxyl groups on aspartic acid and glutamic acid residues in the molecular structure of silk fibroin to form a facilitator-unstable urea derivative, and then reacts with N-hydroxysuccinimide (NHS) to form a more stable ester to enhance the water stability of the carbodiimide cross-linked product, while the carboxyl group is in an activated state at this time. After the carboxyl group is activated, the amino group on the cysteamine hydrochloride reacts with the activated carboxyl group at this time to form an amide bond, and cysteamine is successfully grafted onto the silk fibroin molecule. At the same time, during the reaction, 1-(3-dimethylaminopropyl)-3-ethylcarbodiimide hydrochloride and N-hydroxysuccinimide are converted into water-soluble urea derivatives, which can be removed in the subsequent dialysis process to retain the good biocompatibility of silk fibroin.

The redox potential of the disulfide bond is relatively low, with an apparent reduction potential of about 0.6 volts, and it is easy to undergo a reversible redox reaction. After the silk fibroin is grafted with thiol groups, the thiol groups are oxidized in the presence of oxygen in the air to form disulfide crosslinking points between the silk fibroin molecular chains. The crosslinking points formed by this disulfide bond are reversible, and will be disconnected and turned back into thiol groups under reducing conditions, and the crosslinking points between the molecular chains will be disconnected. In the absence of power, the degree of crosslinking between the silk fibroin molecular chains is high, so that the swelling rate of the silk microneedles is small; while in the power-on state, the current provides a reducing environment, the disulfide bonds obtain electrons to undergo an electrochemical reduction reaction, the disulfide bonds are disconnected to form thiol groups, the covalent crosslinking points between the silk fibroin molecular chains are reduced, and the swelling rate of the silk microneedles is increased. This change in swelling degree can be controlled by switching the power supply. Therefore, an electro-responsive silk fibroin material is obtained, and the purpose of controlling the change in swelling degree is achieved by responding to the current, thereby controlling the release rate of the drug in the microneedle.

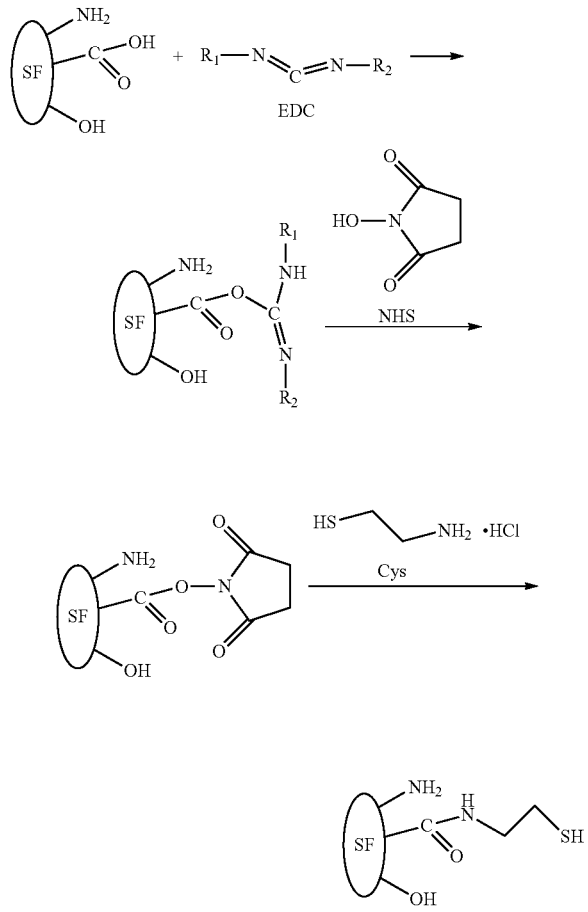

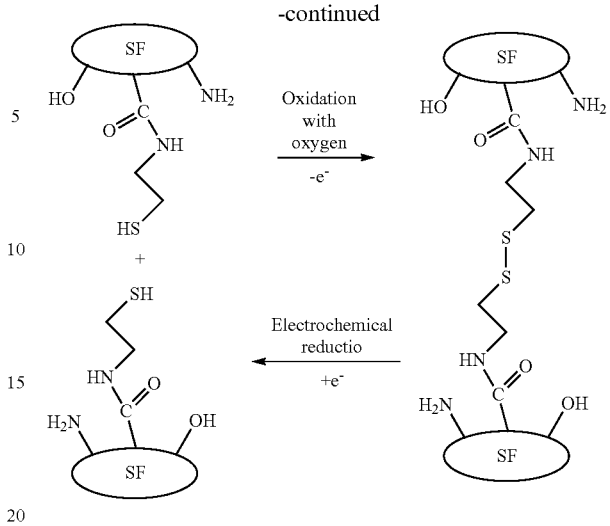

Due to the adoption of the above technical solutions, the present disclosure has the following advantages compared with the prior art: the method for preparing an electro-responsive silk fibroin material of the present disclosure and the prepared electro-responsive silk fibroin material can achieve changes in swelling degree under low voltage stimulation, have high swelling characteristics under power-on conditions, have low swelling characteristics under no power-on conditions, and realize controlled release of drugs.

BRIEF DESCRIPTION OF THE DRAWINGS

In order to more clearly illustrate the technical solutions in the embodiments of the present disclosure, the following briefly introduces the drawings required for use in the description of the embodiments. Obviously, the drawings described below are only some embodiments of the present disclosure. For ordinary technicians in this field, other drawings can be obtained based on these drawings without creative work.

Figure 1:
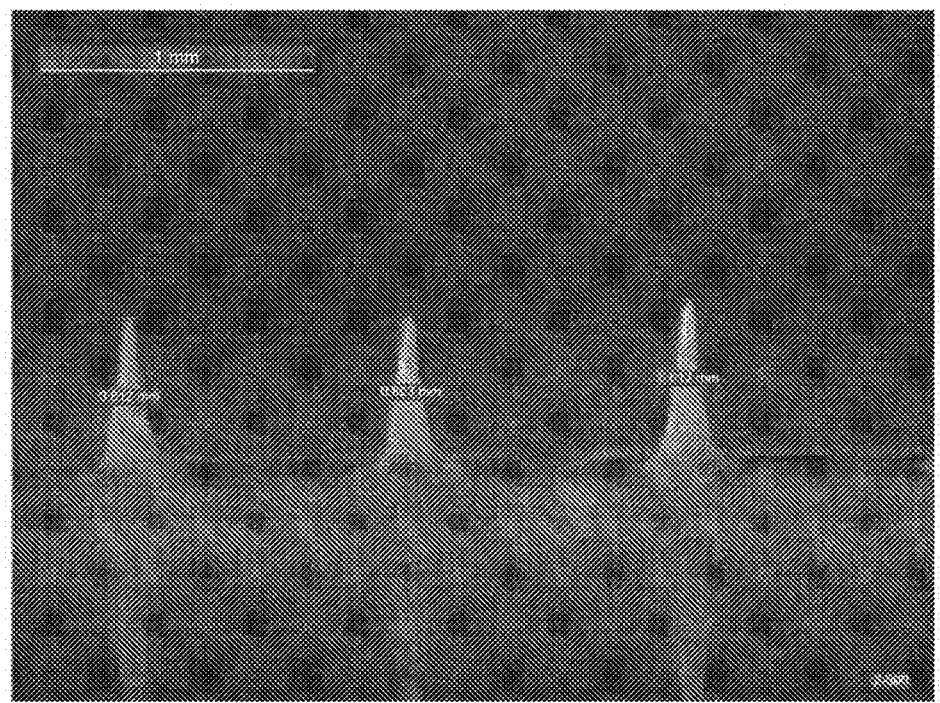
FIG. 1 shows a microscope photograph of the microneedle patch prepared in the preferred embodiment 2 according to the present disclosure.
Figure 2:
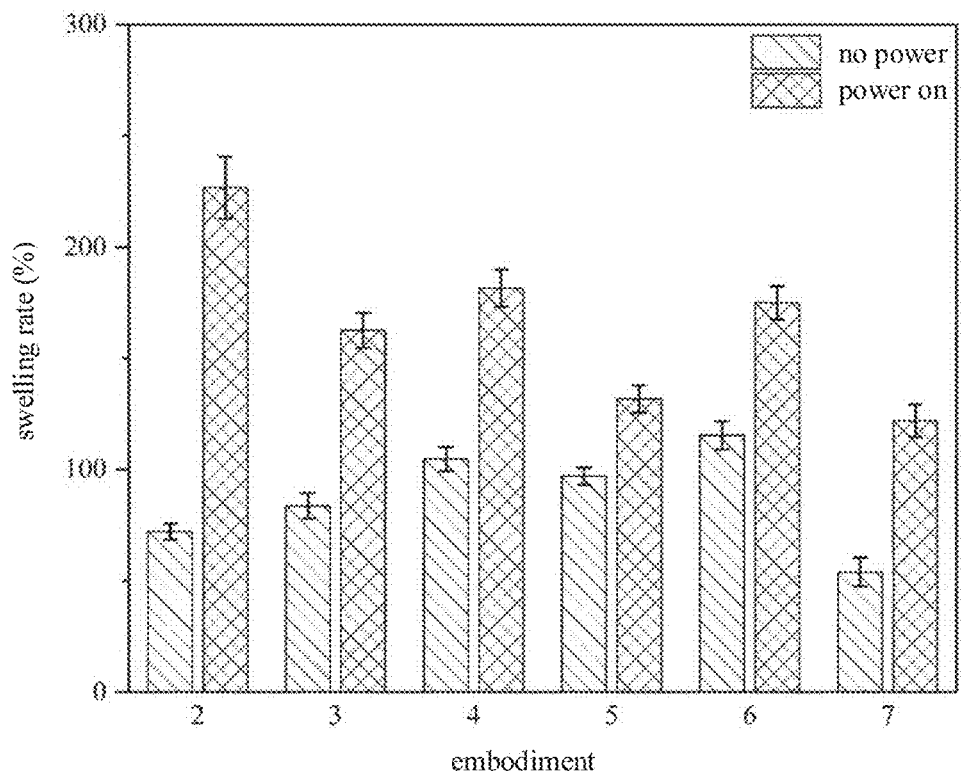
FIG. 2 shows a diagram showing the change in swelling degree of the electro-responsive silk fibroin microneedle patch prepared in embodiment 2-7 of the present disclosure when powered on and not powered on according to the present disclosure.
Figure 3:
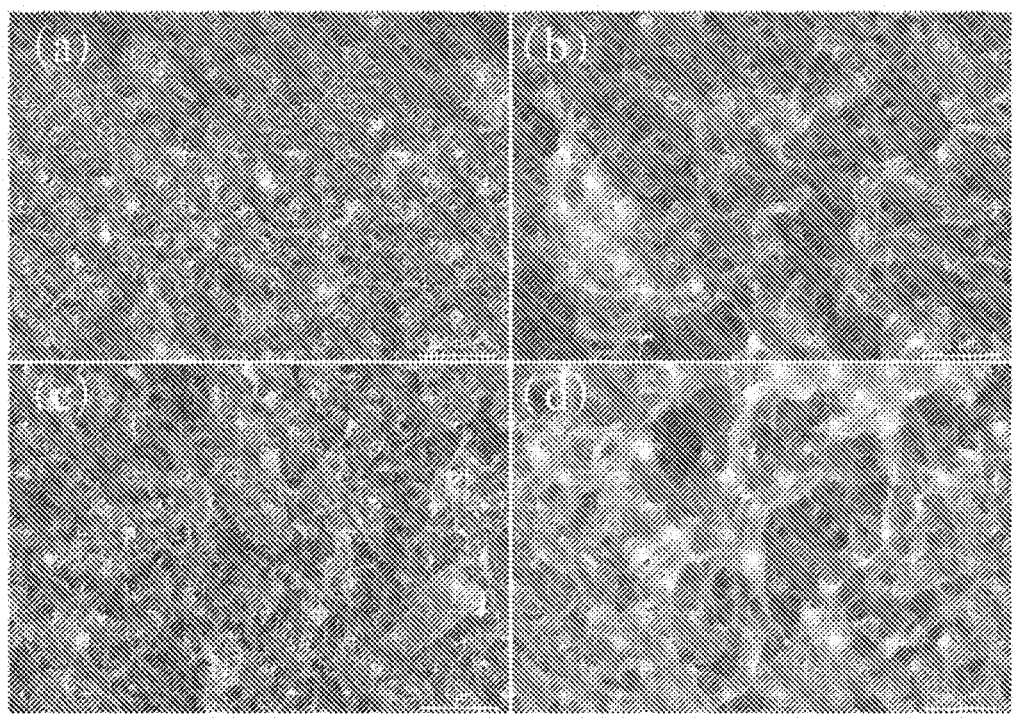
Figure 4:
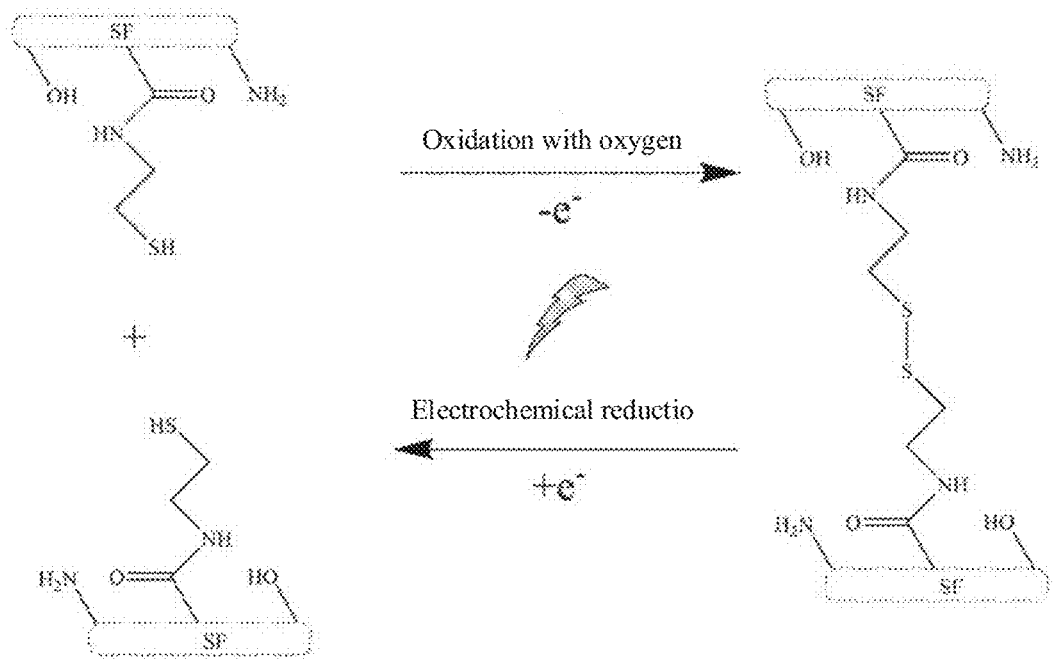
Figure 5:
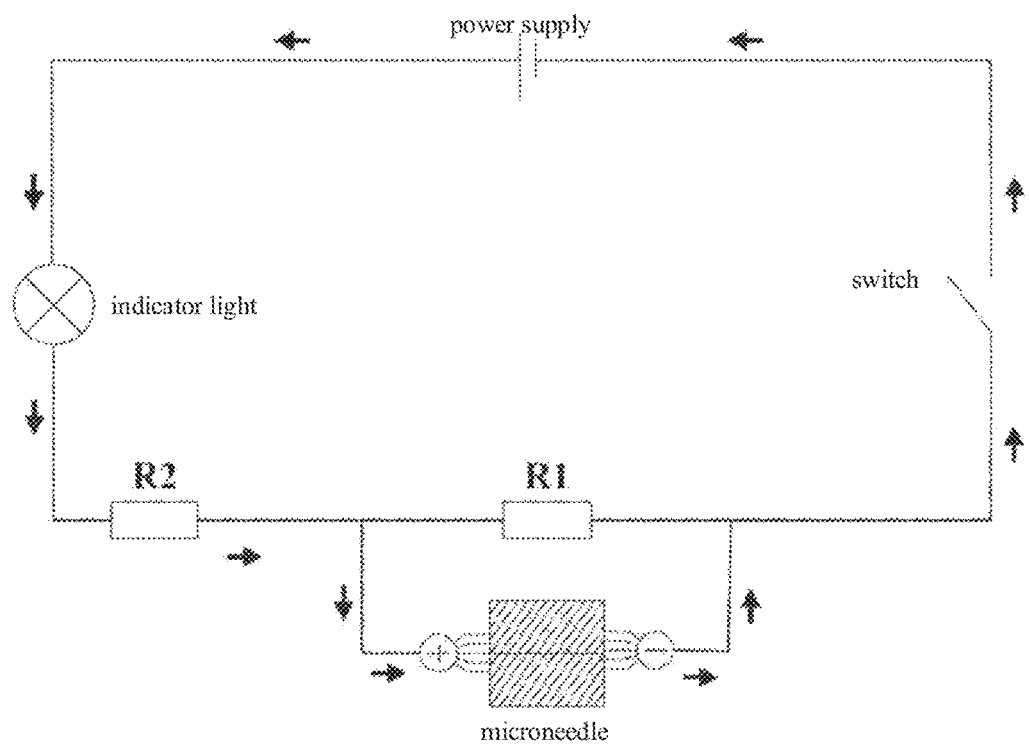

Combining FIG. 2 and embodiment 2-7, it can be seen that excessive addition of N-hydroxysuccinimide and 1-(3-dimethylaminopropyl)-3-ethylcarbodiimide hydrochloride will reduce the current responsiveness and swelling performance of the silk fibroin microneedle patch, and increasing the amount of cysteamine hydrochloride added can increase the swelling degree of the microneedle patch;

FIG. 3 shows a scanning electron microscope image of the internal pore size of the electro-responsive silk fibroin microneedle patch prepared in embodiment 2 of the present disclosure when powered on and not powered on; wherein FIG. 3 (a-b) is an electron microscope image of the internal pore size of the microneedle before power is applied, and FIG. 3 (c-d) is an electron microscope image of the internal pore size of the microneedle after power is applied. It can be seen that after power is applied, the pore size inside the microneedle is enlarged, which is conducive to the passage of drugs;

FIG. 4 shows a schematic diagram of the transformation of thiol and disulfide bonds in the material of the electro-responsive silk fibroin microneedle before and after power on in an embodiment of the present disclosure;

FIG. 5 shows a schematic diagram of the structure of the transdermal drug delivery device in embodiment 8 of the present disclosure; in the figure, R1 is a fixed resistor and R2 is an adjustable resistor.

DETAILED DESCRIPTION

In order to enable those skilled in the art to better understand the technical solution of the present disclosure, the technical solution in the embodiments of the present disclosure will be clearly and completely described below in conjunction with the drawings in the embodiments of the present disclosure. Obviously, the described embodiments are only part of the embodiments of the present disclosure, not all of the embodiments. Based on the embodiments of the present disclosure, all other embodiments obtained by ordinary technicians in this field without creative work should fall within the scope of protection of the present disclosure.

Embodiment 1 Preparation of Silk Fbroin Aqueous Solution

Weigh 3 g $NaHCO_3$ and 1 g $Na_2CO_3$ and dissolve them in 4000 mL deionized water, heat to boiling, put in 80 g silk, keep it at 98° C. for 30 min, take it out and wash it with deionized water. Repeat the above steps three times and place it in a 60° C. oven to dry to obtain degummed silk fiber.

Prepare 9.3 mol/L LiBr solution, take 100 mL of LiBr solution and heat it to 65° C. in a water bath, add 15 g of degummed silk fibroin several times and stir to dissolve, then continue heating and stirring for 40 min. Put the liquid into a dialysis bag and place it in deionized water for 72 h, and replace the deionized water every 2 h. After dialysis, the solution is filtered to obtain a silk fibroin aqueous solution.

Embodiment 2

In this embodiment, a method for preparing an electro-responsive silk fibroin microneedle comprises the following steps:

1) Preparation of Thiolated Silk Fibroin Solution

The silk fibroin aqueous solution is diluted to 30 mg/mL, and then the solution beaker is stabilized in an ice bath at 2° C., and the pH value of the silk fibroin solution is adjusted to 5.5 using 2-(N-morpholino) ethanesulfonic acid solution. First, 5 wt % (relative to the mass of silk fibroin) of N-hydroxysuccinimide is slowly added to the above silk fibroin solution, and then 10 wt % of 1-(3-dimethylamino-propyl)-3-ethylcarbodiimide hydrochloride is added, mixed evenly, and reacted for 0.5 h to activate the carboxyl groups on the silk fibroin.

Slowly add 50 mg/mL cysteamine hydrochloride solution to the above silk fibroin solution, so that the concentration of cysteamine hydrochloride in the final solution is 60 mmol/L and the concentration of silk fibroin is 20 mg/mL, and then use 2-(N-morpholino) ethanesulfonic acid solution to adjust the pH value of the final solution to 5.5. Stir the reaction in an ice bath for 4 h, and then take it out and let it stand in a 4° C. low-temperature refrigerator overnight.

2) Dialysis of Thiolated Silk Fibroin Solution

The silk fibroin solution after the reaction is placed in a dialysis bag (molecular weight cutoff of 8-14 kDa) for dialysis. The dialysis environment is to add a small amount of sodium thiosulfate (0.001 mol/L) to deionized water and pass inert gas $N_2$ for protection. The deionized water with sodium thiosulfate added is replaced every 4 h, and the dialysis procedure 2d is repeated and then dialyzed water without added sodium thiosulfate is used for dialysis 1d. After the dialysis is completed, the supernatant is centrifuged to obtain the grafted modified thiolated silk fibroin solution. The mass concentration (wt %) of the silk fibroin solution is then measured and stored in a 4° C. refrigerator for standby use. The thiol content in the modified silk fibroin solution is 92.9±5.7μmol/g.

3) Preparation of Silk Fibroin Microneedles

Take 1 mL of thiolated silk fibroin solution and pour it into a monolithic PDMS (dimethylsiloxane) microneedle mold. Evacuate in a vacuum drying oven to remove air bubbles and repeat three times. Then place the defoamed mold system in a constant temperature and humidity room (25°° C., 55% RH) and dry it for 8 hours in an air-circulating place. After demolding, the silk fibroin microneedle is obtained. The swelling rate of the microneedle is 72±3.63% for 1 hour without power supply, and 227±13.86% for 1 hour with power supply at a voltage of 0.6V.

Embodiment 2-1

In this embodiment, a method for preparing an electro-responsive silk fibroin insulin microneedle patch comprises the following steps:

The steps and parameters described in embodiment 2 are used to carry out 1) preparation of thiolated silk fibroin solution and 2) dialysis of thiolated silk fibroin solution.

3) Preparation of Insulin Solution

Weigh insulin into a centrifuge tube, add 0.01M hydrochloric acid solution, shake and mix to fully dissolve the insulin, then add 0.02M Tris buffer solution to adjust the pH of the solution to 7.1 and the insulin concentration to 10 mg/mL.

4) Preparation of Mixed Solution

Take the insulin solution prepared in the above step and slowly add it to the thiolated silk fibroin solution, so that the concentration of thiolated silk fibroin in the mixed solution is 20 mg/mL and the concentration of insulin is 5 mg/mL.

5) Preparation of Insulin Microneedle Patch

Take 3.5 mL of the mixed solution and pour it into the microneedle mold. Evacuate in a vacuum drying oven to remove air bubbles. Place the defoamed mold system in a constant temperature and humidity room (25° C., 55% RH) and dry it, and an electro-responsive silk fibroin insulin microneedle is obtained after drying and demolding. When the voltage was 0.6 V, the maximum insulin release rate was 89.03±7.34μ g/h, and the maximum insulin release rate without power was 46.34±7.98μ g/h.

Embodiment 3

In this embodiment, a method for preparing an electro-responsive silk fibroin microneedle comprises the following steps:

1) Preparation of Thiolated Silk Fibroin Solution

The silk fibroin aqueous solution is diluted to 20 mg/mL, and then the solution beaker is stabilized in an ice bath at 3° C., and the pH value of the silk fibroin solution is adjusted to 5 using 2-(N-morpholino) ethanesulfonic acid solution. First, 5 wt % (relative to the mass of silk fibroin) of N-hydroxysuccinimide is slowly added to the above silk fibroin solution, and then 8 wt % of 1-(3-dimethylaminopropyl)-3-ethylcarbodiimide hydrochloride is added, mixed evenly, and reacted for 0.6 h to activate the carboxyl groups on the silk fibroin.

Slowly add 60 mg/mL cysteamine hydrochloride solution to the above silk fibroin solution, so that the concentration of cysteamine hydrochloride in the final solution is 40 mmol/L and the concentration of silk fibroin is 20 mg/mL, and then use 2-(N-morpholino) ethanesulfonic acid solution to adjust the pH value of the final solution to 5. Stir the reaction in an ice bath for 4 h, and then take it out and let it stand in a 4° C. low-temperature refrigerator overnight.

2) Dialysis of Thiolated Silk Fibroin Solution

The silk fibroin solution after the reaction is placed in a dialysis bag (molecular weight cutoff of 8-14 kDa) for dialysis. The dialysis environment is to add a small amount of sodium thiosulfate (0.0015 mol/L) to deionized water and pass inert gas $N_2$ for protection. The deionized water with sodium thiosulfate added is replaced every 4 h, and the dialysis procedure 2d is repeated and then dialyzed water without added sodium thiosulfate is used for dialysis 1d. After the dialysis is completed, the supernatant is centrifuged to obtain the grafted modified thiolated silk fibroin solution. The mass concentration (wt %) of the silk fibroin solution is then measured and stored in a 4° C. refrigerator for standby use. The thiol content in the modified silk fibroin solution is 23.3±2.2µ mol/g.

3) Preparation of Silk Fibroin Microneedles

Take 1 mL of thiolated silk fibroin solution prepared in the above step (2) and pour it into a monolithic PDMS microneedle mold. Evacuate in a vacuum drying oven to remove air bubbles and repeat three times. Then place the defoamed mold system in a constant temperature and humidity room (25° C., 55% RH) and dry it for 6 hours in an air-circulating place. After demolding, the silk fibroin microneedle is obtained. The swelling rate of the microneedle is 84±5.76% for 1 hour without power supply, and 163±7.81% for 1 hour with power supply at a voltage of 0.6V.

Embodiment 3-1

In this embodiment, a method for preparing an electro-responsive silk fibroin insulin microneedle patch comprises the following steps:

The steps and parameters described in embodiment 3 are used to carry out 1) preparation of thiolated silk fibroin solution and 2) dialysis of thiolated silk fibroin solution.

3) Preparation of Insulin Solution

Weigh insulin into a centrifuge tube, add 0.05M hydrochloric acid solution, shake and mix to fully dissolve the insulin, then add 0.01M Tris buffer solution to adjust the pH of the solution to 6.7 and the insulin concentration to 15 mg/mL.

4) Preparation of Mixed Solution

Take the insulin solution prepared in the above step and slowly add it to the thiolated silk fibroin solution, so that the concentration of thiolated silk fibroin in the mixed solution is 20 mg/mL and the concentration of insulin is 3 mg/mL.

5) Preparation of Insulin Microneedle Patch

Take 3.5 mL of the mixed solution and pour it into the microneedle mold. Evacuate in a vacuum drying oven to remove air bubbles. Place the defoamed mold system in a constant temperature and humidity room (25° C., 55% RH) and dry it, and an electro-responsive silk fibroin insulin microneedle is obtained after drying and demolding. When the voltage was 0.6 V, the maximum insulin release rate was 43.08±1.99µ g/h, and the maximum insulin release rate without power was 27.74±2.98µ g/h.

Embodiment 4

In this embodiment, a method for preparing an electro-responsive silk fibroin microneedle comprises the following steps:

1) Preparation of Thiolated Silk Fibroin Solution

The silk fibroin aqueous solution is diluted to 20 mg/mL, and then the solution beaker is stabilized in an ice bath at 2° C., and the pH value of the silk fibroin solution is adjusted to 5.5 using 2-(N-morpholino) ethanesulfonic acid solution. First, 2.5 wt % (relative to the mass of silk fibroin) of N-hydroxysuccinimide is slowly added to the above silk fibroin solution, and then 4 wt % of 1-(3-dimethylaminopropyl)-3-ethylcarbodiimide hydrochloride is added, mixed evenly, and reacted for 0.8 h to activate the carboxyl groups on the silk fibroin.

Slowly add 55 mg/mL cysteamine hydrochloride solution to the above silk fibroin solution, so that the concentration of cysteamine hydrochloride in the final solution is 80 mmol/L and the concentration of silk fibroin is 20 mg/mL, and then use 2-(N-morpholino) ethanesulfonic acid solution to adjust the pH value of the final solution to 5.5. Stir the reaction in an ice bath for 4 h, and then take it out and let it stand in a 4° C. low-temperature refrigerator overnight.

2) Dialysis of Thiolated Silk Fibroin Solution

The silk fibroin solution after the reaction is placed in a dialysis bag (molecular weight cutoff of 8-14 kDa) for dialysis. The dialysis environment is to add a small amount of sodium thiosulfate (0.0015 mol/L) to deionized water and pass inert gas $N_2$ for protection. The deionized water with sodium thiosulfate added is replaced every 4 h, and the dialysis procedure 2d is repeated and then dialyzed water without added sodium thiosulfate is used for dialysis 1d. After the dialysis is completed, the supernatant is centrifuged to obtain the grafted modified thiolated silk fibroin solution. The mass concentration (wt %) of the silk fibroin solution is then measured and stored in a 4° C. refrigerator for standby use. The thiol content in the modified silk fibroin solution is 48.3±2.9µ mol/g.

3) Preparation of Silk Fibroin Microneedles

Take 1 mL of thiolated silk fibroin solution prepared in the above step (2) and pour it into a monolithic PDMS microneedle mold. Evacuate in a vacuum drying oven to remove air bubbles and repeat three times. Then place the defoamed mold system in a constant temperature and humidity room (25° C., 55% RH) and dry it for 6 hours in an air-circulating place. After demolding, the silk fibroin microneedle is obtained. The swelling rate of the microneedle is 105±5.53% for 1 hour without power supply, and 182±8.32% for 1 hour with power supply at a voltage of 0.6V.

Embodiment 4-1

In this embodiment, a method for preparing an electro-responsive silk fibroin insulin microneedle patch comprises the following steps:

The steps and parameters described in embodiment 4 are used to carry out 1) preparation of thiolated silk fibroin solution and 2) dialysis of thiolated silk fibroin solution.

3) preparation of insulin solution

Weigh insulin into a centrifuge tube, add 0.01M hydrochloric acid solution, shake and mix to fully dissolve the insulin, then add 0.01M Tris buffer solution to adjust the pH of the solution to 7.0 and the insulin concentration to 15 mg/mL.

4) Preparation of Mixed Solution

Take the insulin solution prepared in the above step and slowly add it to the thiolated silk fibroin solution, so that the concentration of thiolated silk fibroin in the mixed solution is 30 mg/mL and the concentration of insulin is 2.5 mg/mL.

5) Preparation of Insulin Microneedle Patch

Take 3.5 mL of the mixed solution and pour it into the microneedle mold. Evacuate in a vacuum drying oven to remove air bubbles. Place the defoamed mold system in a constant temperature and humidity room (25° C., 55% RH) and dry it, and an electro-responsive silk fibroin insulin microneedle is obtained after drying and demolding. When the voltage was 0.6 V, the maximum insulin release rate was 34.38±2.74µ g/h, and the maximum insulin release rate without power was 26.64±1.78µ g/h.

Embodiment 5

In this embodiment, a method for preparing an electro-responsive silk fibroin microneedle comprises the following steps:

1) Preparation of Thiolated Silk Fibroin Solution

The silk fibroin aqueous solution is diluted to 25 mg/mL, and then the solution beaker is stabilized in an ice bath at 2° C., and the pH value of the silk fibroin solution is adjusted to 6 using 2-(N-morpholino) ethanesulfonic acid solution. First, 5 wt % (relative to the mass of silk fibroin) of N-hydroxysuccinimide is slowly added to the above silk fibroin solution, and then 7.5 wt % of 1-(3-dimethylaminopropyl)-3-ethylcarbodiimide hydrochloride is added, mixed evenly, and reacted for 0.5 h to activate the carboxyl groups on the silk fibroin.

Slowly add 60 mg/mL cysteamine hydrochloride solution to the above silk fibroin solution, so that the concentration of cysteamine hydrochloride in the final solution is 20 mmol/L and the concentration of silk fibroin is 20 mg/mL, and then use 2-(N-morpholino) ethanesulfonic acid solution to adjust the pH value of the final solution to 6. Stir the reaction in an ice bath for 4 h, and then take it out and let it stand in a 4° C. low-temperature refrigerator overnight.

2) Dialysis of Thiolated Silk Fibroin Solution

The silk fibroin solution after the reaction is placed in a dialysis bag (molecular weight cutoff of 8-14 kDa) for dialysis. The dialysis environment is to add a small amount of sodium thiosulfate (0.001 mol/L) to deionized water and pass inert gas $N_2$ for protection. The deionized water with sodium thiosulfate added is replaced every 4 h, and the dialysis procedure 2d is repeated and then dialyzed water without added sodium thiosulfate is used for dialysis 1d. After the dialysis is completed, the supernatant is centrifuged to obtain the grafted modified thiolated silk fibroin solution. The mass concentration (wt %) of the silk fibroin solution is then measured and stored in a 4° C. refrigerator for standby use. The thiol content in the modified silk fibroin solution is 41.2±3.1µ mol/g.

3) Preparation of Silk Fibroin Microneedles

Take 1 mL of thiolated silk fibroin solution prepared in the above step (2) and pour it into a monolithic PDMS microneedle mold. Evacuate in a vacuum drying oven to remove air bubbles and repeat three times. Then place the defoamed mold system in a constant temperature and humidity room (25° C., 55% RH) and dry it for 6 hours in an air-circulating place. After demolding, the silk fibroin microneedle is obtained. The swelling rate of the microneedle is 97±3.87% for 1 hour without power supply, and 132±6.21% for 1 hour with power supply at a voltage of 0.6V.

Embodiment 5-1

In this embodiment, a method for preparing an electro-responsive silk fibroin insulin microneedle patch comprises the following steps:

The steps and parameters described in embodiment 5 are used to carry out 1) preparation of thiolated silk fibroin solution and 2) dialysis of thiolated silk fibroin solution.

3) Preparation of Insulin Solution

Weigh insulin into a centrifuge tube, add 0.01M hydrochloric acid solution, shake and mix to fully dissolve the insulin, then add 0.04M Tris buffer solution to adjust the pH of the solution to 7.2 and the insulin concentration to 25 mg/mL.

4) Preparation of Mixed Solution

Take the insulin solution prepared in the above step and slowly add it to the thiolated silk fibroin solution, so that the concentration of thiolated silk fibroin in the mixed solution is 25 mg/mL and the concentration of insulin is 4.5 mg/mL.

5) Preparation of Insulin Microneedle Patch

Take 3.5 mL of the mixed solution and pour it into the microneedle mold. Evacuate in a vacuum drying oven to remove air bubbles. Place the defoamed mold system in a constant temperature and humidity room (25° C., 55% RH) and dry it, and an electro-responsive silk fibroin insulin microneedle is obtained after drying and demolding. When the voltage was 0.6 V, the maximum insulin release rate was 42.94±5.21µ g/h, and the maximum insulin release rate without power was 33.78±0.86µ g/h.

Embodiment 6

In this embodiment, a method for preparing an electro-responsive silk fibroin microneedle comprises the following steps:

1) Preparation of Thiolated Silk Fibroin Solution

The silk fibroin aqueous solution is diluted to 30 mg/mL, and then the solution beaker is stabilized in an ice bath at 2° C., and the pH value of the silk fibroin solution is adjusted to 5 using 2-(N-morpholino) ethanesulfonic acid solution. First, 10 wt % (relative to the mass of silk fibroin) of N-hydroxysuccinimide is slowly added to the above silk fibroin solution, and then 2.5 wt % of 1-(3-dimethylaminopropyl)-3-ethylcarbodiimide hydrochloride is added, mixed evenly, and reacted for 0.5 h to activate the carboxyl groups on the silk fibroin.

Slowly add 40 mg/mL cysteamine hydrochloride solution to the above silk fibroin solution, so that the concentration of cysteamine hydrochloride in the final solution is 60 mmol/L and the concentration of silk fibroin is 30 mg/mL, and then use 2-(N-morpholino) ethanesulfonic acid solution to adjust the pH value of the final solution to 5. Stir the reaction in an ice bath for 4 h, and then take it out and let it stand in a 4° C. low-temperature refrigerator overnight.

2) Dialysis of Thiolated Silk Fibroin Solution

The silk fibroin solution after the reaction is placed in a dialysis bag (molecular weight cutoff of 8-14 kDa) for dialysis. The dialysis environment is to add a small amount of sodium thiosulfate (0.0015 mol/L) to deionized water and pass inert gas $N_2$ for protection. The deionized water with sodium thiosulfate added is replaced every 4 h, and the dialysis procedure 2d is repeated and then dialyzed water without added sodium thiosulfate is used for dialysis 1d.

After the dialysis is completed, the supernatant is centrifuged to obtain the grafted modified thiolated silk fibroin solution. The mass concentration (wt %) of the silk fibroin solution is then measured and stored in a 4° C. refrigerator for standby use. The thiol content in the modified silk fibroin solution is 53.3±2.6µ mol/g.

3) Preparation of Silk Fibroin Microneedles

Take 1mL of thiolated silk fibroin solution prepared in the above step (2) and pour it into a monolithic PDMS microneedle mold. Evacuate in a vacuum drying oven to remove air bubbles and repeat three times. Then place the defoamed mold system in a constant temperature and humidity room (25° C., 55% RH) and dry it for 6 hours in an air-circulating place. After demolding, the silk fibroin microneedle is obtained. The swelling rate of the microneedle is 115±6.27% for 1 hour without power supply, and 176±7.53% for 1 hour with power supply at a voltage of 0.6V.

Embodiment 6-1

In this embodiment, a method for preparing an electro-responsive silk fibroin insulin microneedle patch comprises the following steps:

The steps and parameters described in embodiment 6 are used to carry out 1) preparation of thiolated silk fibroin solution and 2) dialysis of thiolated silk fibroin solution.

3) Preparation of Insulin Solution

Weigh insulin into a centrifuge tube, add 0.05M hydrochloric acid solution, shake and mix to fully dissolve the insulin, then add 0.05M Tris buffer solution to adjust the pH of the solution to 7.1 and the insulin concentration to 40 mg/mL.

4) Preparation of Mixed Solution

Take the insulin solution prepared in the above step and slowly add it to the thiolated silk fibroin solution, so that the concentration of thiolated silk fibroin in the mixed solution is 30 mg/mL and the concentration of insulin is 7.5 mg/mL.

5) Preparation of Insulin Microneedle Patch

Take 3.5 mL of the mixed solution and pour it into the microneedle mold. Evacuate in a vacuum drying oven to remove air bubbles. Place the defoamed mold system in a constant temperature and humidity room (25° C., 55% RH) and dry it, and an electro-responsive silk fibroin insulin microneedle is obtained after drying and demolding. When the voltage was 0.6 V, the maximum insulin release rate was 120.19±11.78µ g/h, and the maximum insulin release rate without power was 79.93±7.45µ g/h.

Embodiment 7

In this embodiment, a method for preparing an electro-responsive silk fibroin microneedle comprises the following steps:

1) Preparation of Thiolated Silk Fibroin Solution

The silk fibroin aqueous solution is diluted to 20 mg/mL, and then the solution beaker is stabilized in an ice bath at 2° C., and the pH value of the silk fibroin solution is adjusted to 5.5 using 2-(N-morpholino) ethanesulfonic acid solution. First, 8 wt % (relative to the mass of silk fibroin) of N-hydroxysuccinimide is slowly added to the above silk fibroin solution, and then 20 wt % of 1-(3-dimethylamino-propyl)-3-ethylcarbodiimide hydrochloride is added, mixed evenly, and reacted for 0.5 h to activate the carboxyl groups on the silk fibroin.

Slowly add 50 mg/mL cysteamine hydrochloride solution to the above silk fibroin solution, so that the concentration of cysteamine hydrochloride in the final solution is 60 mmol/L and the concentration of silk fibroin is 20 mg/mL, and then use 2-(N-morpholino) ethanesulfonic acid solution to adjust the pH value of the final solution to 5.5. Stir the reaction in an ice bath for 4 h, and then take it out and let it stand in a 4° C. low-temperature refrigerator overnight.

2) Dialysis of Thiolated Silk Fibroin Solution

The silk fibroin solution after the reaction is placed in a dialysis bag (molecular weight cutoff of 8-14 kDa) for dialysis. The dialysis environment is to add a small amount of sodium thiosulfate (0.001 mol/L) to deionized water and pass inert gas $N_2$ for protection. The deionized water with sodium thiosulfate added is replaced every 4 h, and the dialysis procedure 2d is repeated and then dialyzed water without added sodium thiosulfate is used for dialysis 1d. After the dialysis is completed, the supernatant is centrifuged to obtain the grafted modified thiolated silk fibroin solution. The mass concentration (wt %) of the silk fibroin solution is then measured and stored in a 4° C. refrigerator for standby use. The thiol content in the modified silk fibroin solution is 63.3±4.5µ mol/g.

3) Preparation of Silk Fibroin Microneedles

Take 1 mL of thiolated silk fibroin solution prepared in the above step (2) and pour it into a monolithic PDMS microneedle mold. Evacuate in a vacuum drying oven to remove air bubbles and repeat three times. Then place the defoamed mold system in a constant temperature and humidity room (25° C., 55% RH) and dry it for 6 hours in an air-circulating place. After demolding, the silk fibroin microneedle is obtained. The swelling rate of the microneedle is 55±6.49% for 1 hour without power supply, and 123±7.18% for 1 hour with power supply at a voltage of 0.6V.

Embodiment 7-1

In this embodiment, a method for preparing an electro-responsive silk fibroin insulin microneedle patch comprises the following steps:

The steps and parameters described in embodiment 7 are used to carry out 1) preparation of thiolated silk fibroin solution and 2) dialysis of thiolated silk fibroin solution.

3) Preparation of Insulin Solution

Weigh insulin into a centrifuge tube, add 0.02M hydrochloric acid solution, shake and mix to fully dissolve the insulin, then add 0.01M Tris buffer solution to adjust the pH of the solution to 7.3 and the insulin concentration to 10 mg/mL.

4) Preparation of Mixed Solution

Take the insulin solution prepared in the above step and slowly add it to the thiolated silk fibroin solution, so that the concentration of thiolated silk fibroin in the mixed solution is 30 mg/mL and the concentration of insulin is 1.5 mg/mL.

5) Preparation of Insulin Microneedle Patch

Take 3.5 mL of the mixed solution and pour it into the microneedle mold. Evacuate in a vacuum drying oven to remove air bubbles. Place the defoamed mold system in a constant temperature and humidity room (25° C., 55% RH) and dry it, and an electro-responsive silk fibroin insulin microneedle is obtained after drying and demolding. When the voltage was 0.6 V, the maximum insulin release rate was 16.79±0.96µ g/h, and the maximum insulin release rate without power was 12.62±1.17µ g/h.

Embodiment 8

As shown in FIG. 5, the transdermal drug delivery device in the present embodiment includes a power supply, a switch, an alarm component, a fixed resistor R1, an adjustable resistor R2, a microneedle patch containing a drug, and an electric wire connected between the various components. The power supply, the switch, the alarm component, and the adjustable resistor R2 constitute a main circuit, and the fixed resistor R1 is connected to the main circuit after being connected in parallel with the microneedle patch. That is, the fixed resistor R1 is connected in series with the power supply, the adjustable resistor R2, and the switch after being connected in parallel with the microneedle patch. The alarm component in the present embodiment is an indicator light.

Wherein the power supply is a DC power supply with a voltage range of 3~3.6 V. Various small energy output products can be selected, such as: 3.6V rechargeable lithium-ion button battery (LIR series), 3V rechargeable lithium-ion button battery (ML or VL series), non-rechargeable ones include 3V lithium-manganese button battery (CR series), etc.

The resistance of the fixed resistor R1 is 500Ω; the resistance adjustment range of the adjustable resistor R2 is 200-2000Ω. The fixed resistor R1 and the adjustable resistor R2 are used to maintain the voltage loaded on the microneedle patch within the safe voltage of 0.6~1V. The safe voltage needs to ensure safety in use on the one hand, and on the other hand, it needs to cooperate with the microneedle patch to achieve response.

The microneedle patch used in the present embodiment contains medicine, which is a drug carrier, and can be electrically conductive, for releasing medicine outward when powered on, preferably an electro-responsive microneedle patch, to achieve the controlled release of medicine by the adjustment of matching voltage. By adjusting the resistance value of adjustable resistor R2, the voltage loaded on the microneedle patch can be adjusted to achieve the controlled release of medicine, and fixed resistor R1 is set to ensure safety in use. In particular, the microneedle patch can adopt the microneedle patch form of the conductive polymer microneedle patch containing medicine, the polymer hydrogel of the response electrical stimulation, and is preferably the silk fibroin insulin microneedle patch recorded in the above-mentioned embodiment.

Tests and Results

1) Table 1 shows the thiol content in the silk fibroin microneedles prepared in embodiments 2-7 of the present disclosure and the corresponding swelling rates before and after power on.

The swelling rate test method is as follows: soak in deionized water (37° C.) for 1 hour, and compare the mass increase rate before and after soaking. Swelling rate=(mass after soaking−mass before soaking)/mass before soaking.

TABLE 1

The thiol content in the silk fibroin microneedles in embodiments 2-7 and the corresponding swelling rates before and after power on

| embodiment | 2 | 3 | 4 | 5 | 6 | 7 |
|---|---|---|---|---|---|---|
| thiol content (μmol/g) | 92.9 ± 5.7 | 23.3 ± 2.2 | 48.3 ± 2.9 | 41.2 ± 3.1 | 53.3 ± 2.5 | 63.3 ± 4.5 |
| swelling rate for 1 h without power supply (%) | 72 ± 3.63 | 84 ± 5.76 | 105 ± 5.53 | 97 ± 3.87 | 115 ± 6.27 | 55 ± 6.49 |
| swelling rate for 1 h with power supply at a voltage of 0.6 v (%) | 227 ± 13.86 | 163 ± 7.81 | 182 ± 8.32 | 132 ± 6.21 | 176 ± 7.53 | 123 ± 7.18 |

Combining the results in Table 1 and FIG. 2, it can be seen that the swelling rate of the electro-responsive silk fibroin microneedles prepared in the embodiment increased significantly after power was applied, and the higher the thiol content, the better the swelling effect.

2) Table 2 shows the changes in the thiol content and insulin release rate in the silk fibroin insulin microneedle patch in embodiments 2-1 to 7-1 under powered on and not powered on conditions.

The release rate of insulin was measured and calculated as follows: Franz diffusion cell was used as the in vitro drug receiving cell, 0.01M PBS buffer solution at 32° C. was used as the simulated body fluid, silk fibroin insulin microneedle patch was taken, and the microneedle was inserted into the rat skin by hand. The skin was flatly covered on the round opening of the receiving chamber of the Franz transdermal diffusion cell, the dermis was attached to the receiving chamber, and the donor chamber and the receiving chamber are clamped with stainless steel iron clips to make them stable. The solution in the transdermal drug release cell was sampled every hour, and the concentration of the insulin test sample was detected by HPLC to calculate the insulin release rate.

TABLE 2

Changes in insulin release rate of microneedle patches in embodiments 2-1 to 7-1 under powered on and not powered on conditions

| embodiment | 2-1 | 3-1 | 4-1 | 5-1 | 6-1 | 7-1 |
|---|---|---|---|---|---|---|
| thiol content(μmol/g) | 92.9 ± 5.7 | 23.3 ± 2.2 | 48.3 ± 2.9 | 41.2 ± 3.1 | 53.3 ± 2.5 | 63.3 ± 4.5 |
| insulin content in the mixed solution (mg/mL) | 5 | 3 | 2.5 | 4.5 | 7.5 | 1.5 |

TABLE 2-continued

Changes in insulin release rate of microneedle patches in embodiments 2-1 to 7-1 under powered on and not powered on conditions

| embodiment | 2-1 | 3-1 | 4-1 | 5-1 | 6-1 | 7-1 |
|---|---|---|---|---|---|---|
| maximum release rate (μg/h) | 89.03 ± 7.34 | 43.08 ± 1.99 | 34.38 ± 2.74 | 42.94 ± 5.21 | 120.19 ± 11.78 | 16.79 ± 0.96 |
|  | 46.34 ± 7.98 | 27.74 ± 2.98 | 26.64 ± 1.78 | 33.78 ± 0.86 | 79.93 ± 7.45 | 12.62 ± 1.17 |
| average release rate in 24 h (μg/h) | 41.92 ± 7.11 | 20.85 ± 1.76 | 16.01 ± 2.51 | 21.66 ± 4.98 | 56.60 ± 11.55 | 7.96 ± 0.73 |
|  | 21.93 ± 7.55 | 14.01 ± 2.25 | 12.65 ± 1.55 | 16.04 ± 0.63 | 37.96 ± 7.15 | 5.99 ± 1.02 |

Combined with the results in Table 2, it can be seen that the insulin release rate of the silk fibroin insulin microneedle patch prepared in the above embodiments 2-1 to 7-1 in the powered on state is significantly increased compared to that in the not powered on state, that is, the insulin-containing microneedle patch prepared in the above embodiments can achieve controllable release of insulin.

For the convenience of description and easy understanding, the steps are distinguished and numbered. In actual preparation, the above steps can be carried out simultaneously or in no particular order. In addition, the raw materials not specifically described in the embodiments are all commercially available. Operations without special mention of temperature are carried out at room temperature. The operating methods and conditions not specifically described can adopt the well-known or conventional means and conditions in the art.

In embodiments 2-7, a thiolated silk fibroin is obtained by thiolation of silk fibroin molecules, and then cast to form microneedles. This silk fibroin containing thiol groups will undergo a redox reaction of the thiol groups when current passes through, causing changes in the degree of disulfide crosslinking, thereby responding to the current and forming different swelling states of the silk fibroin. The microneedle transdermal patch prepared by this method has good mechanical properties, biocompatibility, and excellent current-responsive swelling changes, and can achieve controlled drug release under current switching. It can be used in scenarios where the amount of medication needs to be controlled in medical or aesthetic medicine.

In embodiments 2-1 to 7-1, a thiolated silk fibroin is obtained by thiolation of silk fibroin molecules, and the modified silk fibroin solution is mixed with an insulin solution, and then cast in a silicone rubber microneedle mold, and dried after degassing to obtain an electro-responsive silk fibroin insulin microneedle transdermal patch. This thiol-containing silk fibroin undergoes a redox reaction of the thiol when an electric current passes through, causing a change in the degree of crosslinking of disulfide bonds. Thus, in response to the electric current, different swelling states of the silk fibroin are formed, changing the release rate of insulin. The insulin microneedle transdermal patch prepared by this method has good mechanical properties, biocompatibility and excellent current responsiveness, can achieve electro-responsive insulin controlled release, and meet the control of blood sugar before and after eating of patients.

The above embodiments are only for illustrating the technical concept and features of the present disclosure, and their purpose is to enable people familiar with this technology to understand the contents of the present disclosure and implement them accordingly. They cannot be used to limit the protection scope of the present disclosure. All equivalent changes or modifications made according to the spirit of the present disclosure should be included in the protection scope of the present disclosure.

The invention claimed is:

1. A method for preparing an electro-responsive silk fibroin material, comprising:
    (1) activation of silk fibroin: diluting an aqueous solution of silk fibroin to a concentration of 20-30 mg/mL, then stabilizing the temperature of the solution to 0-4° C., and adjusting the pH value of the silk fibroin solution to 5-6 using a buffer solution; adding 1-10 wt % of N-hydroxysuccinimide relative to the mass of the silk fibroin to the silk fibroin solution, and then adding 2-20 wt % of 1-(3-dimethylaminopropyl)-3-ethylcarbodiimide hydrochloride relative to the mass of the silk fibroin, mixing uniformly and performing a reaction for 0.4-1h to obtain an activated silk fibroin solution;
    (2) thiolation of silk fibroin: adding a cysteamine hydrochloride solution dropwise with a concentration of 40-60 mg/mL to the activated silk fibroin solution until the cysteamine hydrochloride concentration in the final solution is 20-80 mmol/L, and then adjusting the pH value of the final solution to 5-6 using a buffer solution; performing a reaction comprising stirring the final solution at a predefined revolutions per minute (RPM) at a temperature of 0-4° C. for 2-5 h, and then letting the resulting product to stand in an environment with a temperature of 2-8° C. for 8-10 h to obtain a thiolated silk fibroin solution;
    (3) purification of thiolated silk fibroin: placing the silk fibroin solution after the reaction in a dialysis bag for dialysis; centrifuging and taking the supernatant to obtain the purified thiolated silk fibroin solution after the dialysis is completed;
    (4) preparation of electro-responsive silk fibroin material: taking the purified thiolated silk fibroin solution, and pouring the purified thiolated silk fibroin solution in a mold, and removing air bubbles by vacuuming; then placing the defoamed mold in a constant temperature and humidity environment for drying, wherein the constant temperature and humidity conditions are 20-30° C. and 55-65% relative humidity, and obtaining the electro-responsive silk fibroin material after drying and demolding;
    wherein the electro-responsive silk fibroin material contains thiol groups; the thiol content of the electro-responsive silk fibroin material is 20-100 μmol/g;
    wherein sodium thiosulfate is added to deionized water for dialysis and an inert gas is introduced into the deionized water to prevent oxidation of the sodium thiosulphate during the dialysis; the deionized water with added sodium thiosulfate is replaced with a fresh batch of deionized water with sodium thiosulfate every 2-4 h, and the dialysis procedure is repeated and the inert gas protection is maintained in a first stage; then the deionized water without added sodium thiosulfate is used for dialysis in a second stage;

wherein the swelling rate of the silk fibroin material is 50-120% when the silk fibroin material is not powered on, and 120-250% when powered on at a voltage of 0.6V.

2. A method for preparing an electro-responsive silk fibroin material according to claim 1, wherein the mass ratio of the N-hydroxysuccinimide to the silk fibroin is 1:100-1:10; the mass ratio of the 1-(3-dimethylaminopropyl)-3-ethylcarbodiimide hydrochloride to the silk fibroin is 1:50-1:5; the mass ratio of the cysteamine hydrochloride to the silk fibroin is 1:100-1:2.5.

3. A method for preparing an electro-responsive silk fibroin material according to claim 1, wherein the buffer solution is one selected from 2-(N-morpholino) ethanesulfonic acid, glycine-hydrochloric acid, citric acid-sodium citrate, acetic acid-sodium acetate, potassium hydrogen phthalate-sodium hydroxide, and Tris-hydrochloric acid buffer.

4. A method for preparing an electro-responsive silk fibroin material according to claim 1, wherein the silk fibroin aqueous solution is obtained from silkworm silk through degumming, dissolution and dialysis.

5. A method for preparing an electro-responsive silk fibroin material according to claim 1, wherein the electro-responsive silk fibroin material is an electro-responsive silk fibroin microneedle.

\* \* \* \* \*